United States Patent [19]

McLeod et al.

[11] Patent Number: 5,456,722
[45] Date of Patent: Oct. 10, 1995

[54] LOAD BEARING POLYMERIC CABLE

[75] Inventors: William D. McLeod; James J. Cassidy, both of Memphis, Tenn.

[73] Assignee: Smith & Nephew Richards Inc., Memphis, Tenn.

[21] Appl. No.: 100,458

[22] Filed: Jul. 30, 1993

Related U.S. Application Data

[63] Continuation of Ser. No. 1,065, Jan. 6, 1993.

[51] Int. Cl.⁶ .................................................. A61F 2/08
[52] U.S. Cl. .............................. 623/13; 623/17; 606/228
[58] Field of Search ................................... 623/1, 13, 17, 623/66; 606/224, 228; 87/6, 8

[56] References Cited

U.S. PATENT DOCUMENTS

| | | |
|---|---|---|
| 3,176,316 | 1/1963 | Bodell . |
| 3,613,120 | 10/1971 | McFarland, Jr. . |
| 4,034,763 | 7/1977 | Frazier . |
| 4,074,366 | 2/1978 | Capozza . |
| 4,127,902 | 12/1978 | Homsy . |
| 4,149,277 | 4/1979 | Bokros . |
| 4,187,558 | 2/1980 | Dahlen et al. . |
| 4,209,859 | 7/1980 | Hoffman . |
| 4,246,660 | 1/1981 | Wevers . |
| 4,255,820 | 3/1981 | Rothermel et al. . |
| 4,301,551 | 11/1981 | Dore et al. . |
| 4,345,339 | 8/1982 | Muller et al. . |
| 4,413,110 | 11/1983 | Kavesh et al. . |
| 4,455,690 | 6/1984 | Homsy . |
| 4,483,023 | 11/1984 | Hoffman, Jr. et al. . |
| 4,512,038 | 4/1985 | Alexander et al. . |
| 4,584,722 | 4/1986 | Levy et al. . |
| 4,585,458 | 4/1986 | Kurland . |
| 4,605,414 | 8/1986 | Czajka . |
| 4,608,428 | 8/1986 | Shalaby et al. . |
| 4,610,688 | 9/1986 | Silvestrini et al. . |
| 4,662,886 | 5/1987 | Moorse et al. . |
| 4,668,233 | 5/1987 | Seedhom et al. . |
| 4,728,329 | 3/1988 | Mansat . |
| 4,731,084 | 3/1988 | Dunn et al. ............................. 623/13 |
| 4,775,380 | 10/1988 | Seedhom et al. . |
| 4,776,851 | 10/1988 | Bruchman et al. . |
| 4,792,336 | 12/1988 | Hlavacek et al. ...................... 623/13 |
| 4,795,466 | 1/1989 | Stuhmer et al. . |
| 4,804,383 | 12/1989 | Rey et al. ............................. 623/13 |
| 4,834,752 | 5/1989 | Van Kampen . |
| 4,836,205 | 6/1989 | Barrett . |
| 4,863,471 | 9/1989 | Mansat . |
| 4,870,055 | 9/1989 | Urry et al. . |
| 4,883,486 | 11/1989 | Kapadia et al. . |
| 4,917,699 | 4/1990 | Chervitz ................................ 623/13 |
| 4,917,700 | 4/1990 | Aikins . |
| 4,932,972 | 6/1990 | Dunn et al. ............................. 623/13 |
| 4,942,875 | 7/1990 | Hlavacek et al. . |
| 4,946,377 | 8/1990 | Kovach . |
| 4,979,956 | 12/1990 | Silvestrini . |
| 4,991,763 | 2/1991 | Storace ................................ 227/19 |
| 5,004,474 | 4/1991 | Fronk et al. . |
| 5,019,093 | 5/1991 | Kaplan et al. . |
| 5,061,283 | 10/1991 | Silvestrini . |

FOREIGN PATENT DOCUMENTS

| | | |
|---|---|---|
| 0299858 | 1/1989 | European Pat. Off. . |
| 0317408 | 4/1989 | European Pat. Off. . |
| 0223370 | 5/1991 | European Pat. Off. . |
| 0238223 | 5/1991 | European Pat. Off. . |
| 0153831 | 5/1991 | European Pat. Off. . |
| WO89/01320 | 2/1989 | WIPO . |

OTHER PUBLICATIONS

"Search goes on for thoughest MRI–compatible spine wire", Orthopedics Today, Jun. 1993, vol. 13, No. 6., pp. 20–21.

Primary Examiner—Gary Jackson
Attorney, Agent, or Firm—Pravel, Hewitt, Kimball & Krieger

[57] ABSTRACT

A surgical cable for use in the repair of fractures or fusions of small bones and to assist in the repair of torn ligaments and tendons. The surgical cable has unique characteristics of high tensile strength, flexibility and inelasticity or stiffness.

21 Claims, 3 Drawing Sheets

LOAD BEARING POLYMERIC CABLE

This is a continuation of application Ser. No. 08/001,065 filed Jan. 6, 1993 pending.

FIELD OF THE INVENTION

The present invention relates to a load bearing polymeric surgical cable, more specifically to a stress-sharing/shielding cable or suture for use in the repair of small bone fractures and fusions and in the repair of ligaments and tendons.

BACKGROUND OF THE INVENTION

Surgical procedures for the repair or fusion of small bones, ligaments and tendons, require use of a prosthetic or orthotic device or suture which can bear a heavy load caused by the unique anatomical features of the compromised bone or tendon. For example, fractures of the patella are exposed to high stresses during flexion and extension of the knee joint; fusions of the spinal vertebrae are exposed to high gravitational forces and movements of the spinal column; and torn ligaments and tendons are exposed to high stresses due to contraction of the associated muscles or flexion and extension of the bony structures.

An orthotic, prosthetic device or suture used in such fashion must be able to bear heavy stress loads, be flexible enough to achieve the desired repair, and be sufficiently inelastic to maintain alignment of the anatomical structures for proper fusion and repair.

Materials currently available for such surgical procedures include synthetic or wire sutures, metal cable and various specialized prosthetic or orthotic devices. Synthetic and metal sutures are susceptible to fatigue and breakage during application and use. The currently available synthetic suture materials have insufficient strength and stiffness to provide the stress sharing and strain-limiting capabilities required. Metal cable or wire sutures, while providing additional strength, lack the flexibility required for many fusion and/or repair procedures.

Satisfactory repair or fusion requires that the bones or bone fragments remain sufficiently immobilized to permit healing. Current procedures for the repair or fusion of small bones including vertebrae and the patella, restrict motion of the bones or bone fragments by wiring the elements into the appropriate position. The applied surgical wire is generally bent tightly around the bone fragments and two ends of the wire are generally twisted together to provide compressive force.

Breakage of wire sutures or cables may occur with bending during implantation of the device or post-implantation movement generating repetitive bending stresses. Failure of the wire to supply sufficient compressive force and apposition of bone fragments results in reduced or failed healing of the bones. Sharp wire points caused by wire breakage in situ can result in significant damage to surrounding tissues and/or joint capsules.

Metal suture material is radiopaque, and interferes with efficient X-ray monitoring of bone fusion and repair. Metal sutures also interfere with the use of magnetic resonance imaging diagnostic procedures which require that no metal be present in the vicinity of use.

It would be highly desirable to provide a small diameter, flexible, load bearing suture to replace low strength polymeric or synthetic sutures and metal sutures for use in the fusion, repair, and augmentation of small bones, ligaments, and tendons.

SUMMARY OF THE INVENTION

It has been found that a braided-cable formed of strong polymeric fibers produces a load bearing suture of sufficient tensile strength, flexibility and stiffness to be useful in the repair and fusion of small bones, ligaments and tendons.

The polymeric braided cable of the present invention has strength at least equivalent to that of a metal suture, and much greater flexibility. The present invention does not exhibit the problems associated with metal fatigue and breakage of wire, and may be formed with a much smaller diameter.

The polymeric braided cable of the present invention may also be formed of a bioresorbable polymer, eliminating the necessity of removing the cable and allowing gradual transfer of stress to the tissue or bone over time.

The load bearing cable of the present invention has the following characteristics: greater tensile strength than available polymeric suture materials; greater stiffness than available suture materials; greater flexibility and fatigue lifetime than metal sutures; transparent to x-rays and does not interfere with magnetic resonance imaging; tightly woven to discourage tissue ingrowth.

The load bearing cable of the present invention is formed of a plurality of high tensile strength polymeric fibers, each of which is less than 100 microns in diameter and has a tensile strength of greater than or equal to about 350,000 psi, and preferably greater than 500,000 psi. To form the load-bearing cable, a plurality of such fibers are formed into a hollow braid having a longitudinal bore extending through the center. The load bearing cable may be formed from as few as one ply or as many as six ply bundles of approximately 120 individual fibers per ply. Preferred is a two-ply, eight strand braided cable preferably less than 3 mm in diameter and most preferred is a one ply, eight strand braided cable less than 1 mm in diameter.

BRIEF DESCRIPTION OF THE DRAWINGS

The present invention can be better understood by reference to the drawings in which.

DETAILED DESCRIPTION OF THE EXEMPLARY EMBODIMENTS

FIGS. 1 through 6 illustrate the exemplary embodiments of a load bearing cable 10 of the present invention. Although the cable of the present invention is shown as connecting specific small bones and/or ligaments, the cable can also be used in the repair of other small bones and soft tissues.

Figure 5:
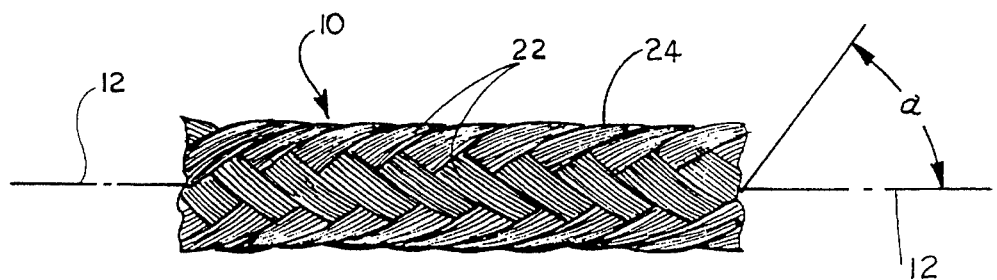
FIG. 5 is a longitudinal view of a braided load bearing cable of the present invention.

As shown in FIG. 5, the load bearing, braided cable 10 is formed of a plurality of biocompatible polymeric fibers wound as bundles of parallel fibers into yarns 22. Yarns of from one to six ply are then wound into strands 24. The strands are then intertwined to form the braided cable 10, for example, an eight-strand diamond braid. In a preferred embodiment, the polymeric fibers are bundled into yarns of approximately 650 denier, the yarns are wound into 1 to 6 ply, and more preferably one or two-ply strands, and the strands are braided into a single, hollow, plain 8-strand diamond braid. The braided construction allows utilization of high strength fibers as individual units while providing negligible bending resistance. Preferably, the resulting braid contains approximately 4 to 8 picks per inch.

In rope terminology, a plain braid is defined according to the number of picks per inch. A "pick" is defined as a crossing of one yarn bundle over another, with the number of picks counted across the longitudinal axis. The greater number of picks per inch, the tighter the braid. In the preferred embodiment, a braid having approximately 4 to 8 picks per inch provides a flexible cable having a desired diameter of less than 3 mm.

The fibers are formed of a high strength, biocompatible, organic polymer, preferably polyolefins such as high strength polypropylene or ultra-high molecular weight polyethylene. U.S. Pat. No. 4,413,110, to Kavesh et. al, which is hereby incorporated by reference, describes one process for the production of ultra-high molecular weight polyethylene (UHMWPE) fibers which have a high tenacity and a high tensile modulus. Any suitable means for providing UHMWPE will suffice.

Commercial embodiments of the polyethylene fibers described in the Kavesh patent known by the trademarks SPECTRA-900 and SPECTRA-1000 and are sold by Allied-Signal, Inc. These commercially available fibers have a tensile strength of about 375,000–425,000 psi per individual monofilament. The density of each monofilament is between 0.5 and 1.5 g/cc, preferably about 0.97. Fibers of SPECTRA-1000 have a tenacity of approximately 35 g/denier, a specific gravity of 0.97 and an average diameter of 27 microns (0.0011 inch). Each monofilament is less than 100 microns in diameter.

Fibers are assembled to form a tight weave which discourages fibrous ingrowth. Preferably, pore sizes are less than 30 microns. For UHMWPE, the cable 10 is optimally formed of 8 strands, each strand having from one to six ply. Each single ply strand contains approximately 120 fibers of UHMWPE. Thus, the preferred embodiment of the braided load-bearing cable 10 has from 960 individual fibers for a one ply braid to 1920 individual fibers for a two ply braid.

Preferably the load bearing cables of the present invention have a diameter of approximately less than three millimeters and can carry loads of up to 550 pounds. For example, a single ply 8-strand diamond braid can withstand a load of approximately 180 lbs. and a double ply can withstand a load of approximately 320 lbs.

The cables of the present invention are formed with the strongest available biocompatible polymer and optionally with a biocompatible resorbable polymer. The upper limit imposed on the strength of the polymer is the flexibility required.

In one embodiment, the polymeric fibers of the present invention are bioresorbable. Suitable fibers are, for example, those formed of polylactic acid or polyglycolic acid.

Examples of materials useful in the present invention are ultra-high molecular weight polyethylene fibers, each having a tensile strength of at least 350,000 psi. Especially preferred is the ultra-high molecular weight polyethylene, e.g., Spectra-1000. The surface of the fibers may be modified, for example roughened, for ease of fixation of the cable.

Figure 6:
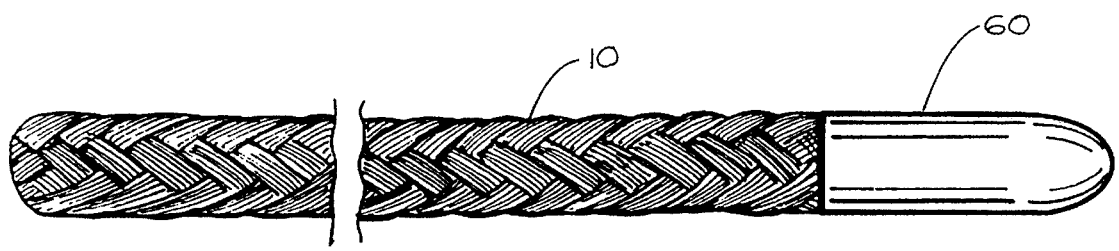
FIG. 6 is a pictorial view of a load bearing cable of the present invention swaged to a needle.

The load bearing cable of the present invention may be utilized in a variety of surgical procedures to fuse or repair small bones and ligaments and tendons. For example, the cable may be used as an orthosis and shield the torn ligament or tendon from the normal stress and strain until the tissue has healed, e.g. by sewing the cable through remnants of a ligament and bringing the torn ends into opposition. To facilitate such use, the cable 10 may be attached to a needle 60 as shown in FIG. 6, or similar device for threading the cable 10 through tissues.

Alternatively, the cable may be used to shield normal stress and strain until the tissue has become strong enough to carry the full amount of stress, e.g. by sewing the cable through a replacement tissue graft. The load bearing cable of the present invention may also be substituted for surgical wire or cable in the repair of small bone fractures such as the patella or bone fusions such as vertebral fusions. The cable has sufficient tensile strength to maintain bone fragments in close approximation to promote active healing and is sufficiently inelastic to prevent separation of fragments under tensile loading. The load bearing cable is less susceptible to fatigue failure than surgical wire. In the event the cable does fail, no threat of damage to surrounding tissue is posed.

Characteristics of the structure of the present invention and its application may be better understood by reference to the examples which follow:

EXAMPLE 1

FATIGUE TESTING OF METAL SURGICAL SUTURES

Titanium orthopedic cable having a diameter of 0.045 inch and cobalt chromium orthopedic cable having a diameter of 0.045 inch were tested for bending fatigue. A 15 inch length of the metal cable was installed on a bending fixture for fatigue testing. A loading rod was fixed to a load cell and the fatigue test fixture was positioned so that the loading rod was directly above the cable. Operating in stroke control the loading rod was moved downward against the cable until a load of two pounds was read. The displacement of the crosshead at this two pound load was recorded. The rod was then advanced until a load of 20 pounds was indicated, and this displacement was recorded. Still in stroke control, a sinusoidal function varying between the two previously recorded displacements was established at a rate of 0.5 Hz. This created a load variation on from 2 to 20 pounds on the cable, with resultant bending around the rod. Testing continued until the cable broke. This testing was performed on six titanium cables and six cobalt chromium cables. The results are shown in Table 1.

TABLE 1

| CABLE MATERIAL | AVG CYCLES TO FAILURE |
|---|---|
| COBALT CHROMIUM | 18,408 (S.D. 4854) |
| TITANIUM | 8,042 (S.D. 1161) |

EXAMPLE 2

FATIGUE TESTING OF A COBALT-CHROME SURGICAL CABLE

Testing was performed on a cobalt-chrome surgical cable (Richards MP35N), 0.044 inches in diameter in a bending fixture as described for Example 1. The pulley system was cycled at a rate of 0.7 Hz at displacements that resulted in the plunger seeing an axial load that varied between 2 to 20 pounds. Cycling was halted upon failure. The average fatigue life was 56,700 cycles.

EXAMPLE 3

FATIGUE TESTING OF BRAIDED UHMWPE SURGICAL CABLE

An ultra-high molecular weight polyethylene braided cable was fabricated from Spectra 1000™ fiber. Yarns of approximately 650 denier were arranged as single ply and two-ply strands, and braided into an 8-strand hollow diamond braid.

The braided cable was fatigue tested in a bending fixture as described in Example 1. The springs had a spring constant of 6 lbs/in. The pulley radius was one inch. The distance between pulley centers was three inches. The load plunger had a radius of 0.2 inches. Each test was conducted at 1 Hz.

During fatigue testing, the surgical cable or metal suture was subjected to a sinusoidal plunger load of from 2–20 pounds-force (lbf). The springs provided resistance to the plunger load. The material was also subjected to a pre-load of approximately 7.5 lbf due to the tensioning of the springs.

The polymeric ultra high molecular weight polyethylene cable of the present invention was attached to the springs by tying a knot in both ends of the braid and searing the knot with heat. The knot was then passed through a ring and set screw and a set screw was tightened down to secure the braid to the spring.

Because the cable was flexible, the loading was considered a purely tensile load. Therefore, a static analysis was used to determine the tension in the cable. A single ply braid having a cross-sectional diameter of approximately 0.040 inches (1 mm) and a two-ply braid having a cross-sectional diameter of approximately 0.060 inches (1.52 mm) were tested. The maximum stress in each cable was 401 psi for the single ply and 267 psi for the two ply cables.

Before testing, half of the ultra high molecular weight polyethylene braids were treated to roughen the surface of the braid for enhancement of knot holding capability of the braid by application of a charged plasma to the surface of the braid.

Five tests were run for each of the single ply and two ply braids in both treated and untreated conditions. The results are shown in Table 2. The single ply and two ply braided ultra high molecular weight polyethylene surgical cable in both treated and untreated conditions survived 100,000 cycles in the bending fixture described above. There were no braid failures or knot failures in any of the tests taken to 100,000 cycles.

Fatigue testing of metal surgical cables using the same procedure and protocol indicated that MP35N cables (cobalt-chrome) had a fatigue life of 56,700 cycles as discussed in Example 2. Testing of titanium and Co—Cr surgical cable using the same protocol and procedures determined the fatigue life to be 8,042 cycles and 18,408 cycles, respectively, as discussed in Example 1.

These results indicate the braided polymeric cable of the present invention has a better fatigue life than the metal cables formed of cobalt-chrome, or titanium. The charged plasma surface toughening treatment did not effect the fatigue life of the braid.

TABLE 2

FATIGUE STRENGTH OF UHMWPE BRAIDED CABLE

| PLY | ROUGHENING TREATMENT | CYCLES |
|---|---|---|
| SINGLE | UNTREATED | 100,000 |
| SINGLE | UNTREATED | 100,000 |
| SINGLE | UNTREATED | 100,000 |
| SINGLE | UNTREATED | 100,000 |
| SINGLE | UNTREATED | 100,000 |
| SINGLE | TREATED | 100,000 |
| SINGLE | TREATED | 100,000 |
| SINGLE | TREATED | 100,000 |
| SINGLE | TREATED | 100,000 |
| SINGLE | TREATED | 100,000 |
| TWO-PLY | UNTREATED | 100,000 |
| TWO-PLY | UNTREATED | 100,000 |
| TWO-PLY | UNTREATED | 100,000 |
| TWO-PLY | UNTREATED | 100,000 |
| TWO-PLY | UNTREATED | 100,000 |
| TWO-PLY | TREATED | 100,000 |
| TWO-PLY | TREATED | 100,000 |
| TWO-PLY | TREATED | 100,000 |
| TWO-PLY | TREATED | 100,000 |
| TWO-PLY | TREATED | 100,000 |

EXAMPLE 4

REPAIR OF ANTERIOR CRUCIATE LIGAMENT

The anterior cruciate ligament of the knee connects the femur to the tibia, preventing the tibia from sliding anteriorly beneath the femur. As shown, for example in FIG. 3, to repair or reconstruct a torn anterior cruciate ligament, the load bearing cable 10 of the present invention is anchored to both the femur 30 and the tibia 32. Anchorage to bone may be via surgical staple, pins, or screws 34. The cable 10 is sewn along the axis of the normal ligament, and thus bears all or part of the tensile load normally borne by the native ligament. The cable replaces a cast, castbrace or brace normally required to immobilize the joint after surgery and permits healing of the tissue graft by acting as an internal splint to shield the tissue from stress while permitting some joint motion during the post-operative period. This procedure alleviates loss of tensile strength in the tissue graft normally associated with joint immobilization following surgery. Once satisfactory tissue strength is achieved in the graft, the cable may be removed.

When a bioresorbable cable is used to augment the ligament, the cable will resorb over a suitable time for healing, gradually transferring load to the tissue graft.

EXAMPLE 5

REPAIR OF PATELLA FRACTURE

Figure 1:
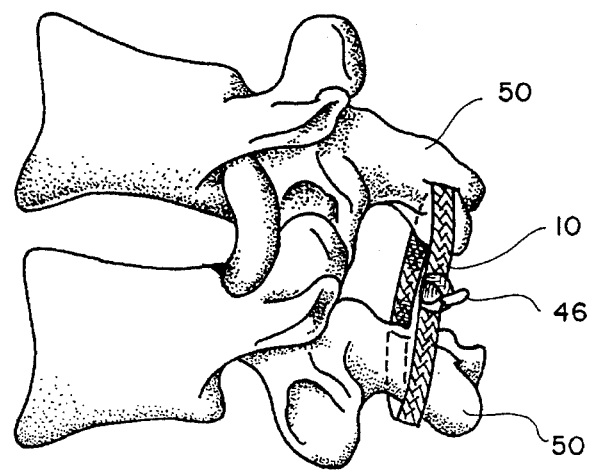
FIG. 1 is a pictorial view of the load bearing cable of the present invention as applied to adjacent vertebrae in a spinal column fusion.
Figure 2:
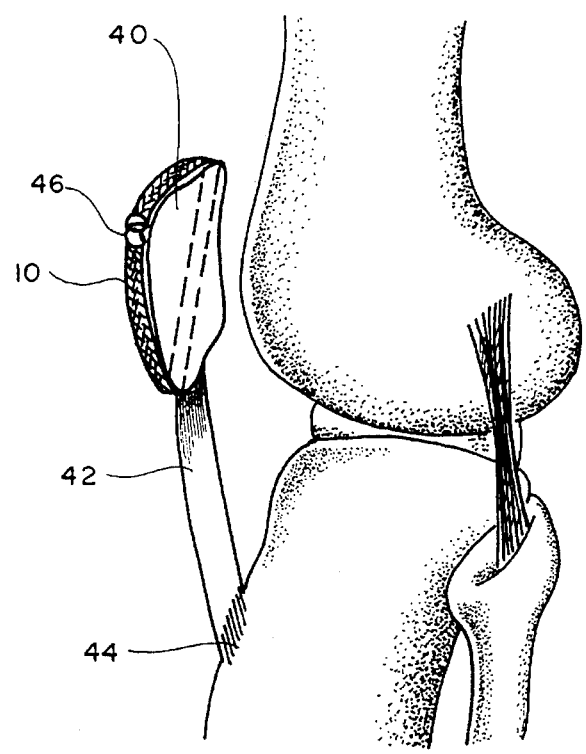
FIG. 2 is a pictorial view of the load bearing cable of the present invention as applied to repair of a fractured patella.
Figure 3:
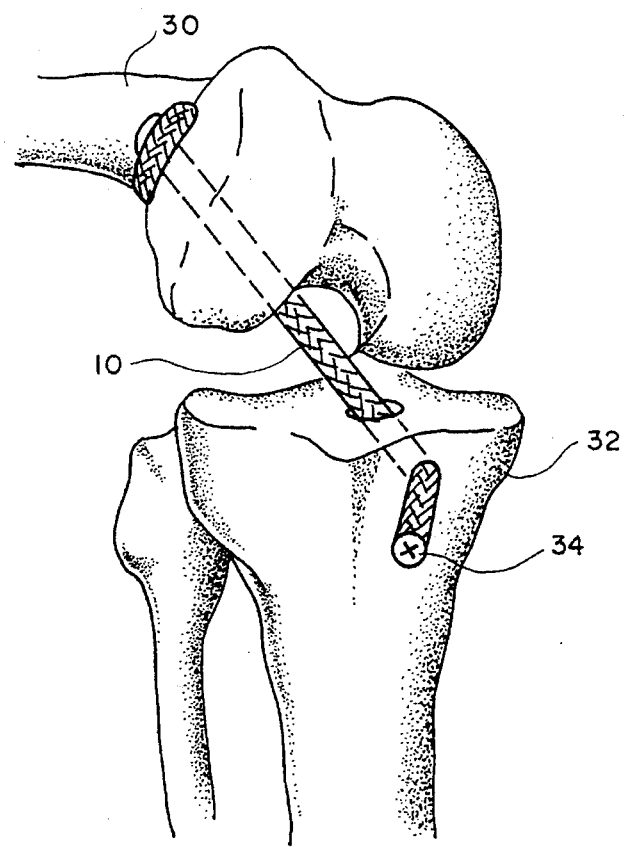
FIG. 3 is a pictorial view of the load bearing cable of the present invention as applied to the repair of a torn ligament.
Figure 4:
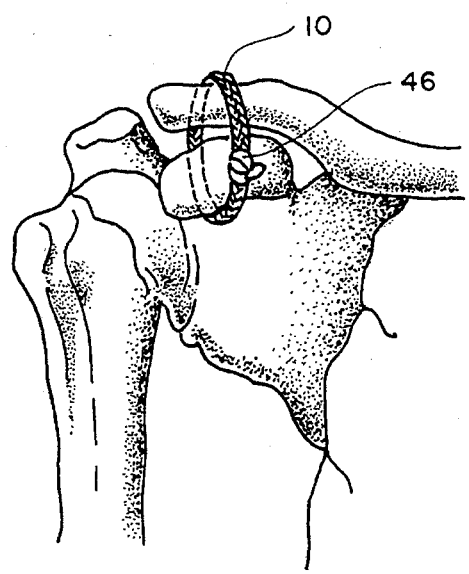
FIG. 4 is a pictorial view of the load bearing cable of the present invention as applied to the repair of a clavicular ligament.

As shown in FIG. 2, the patella 40 is a small bone which covers the anterior compartment of the knee joint. Superiorly it is attached to the tendon of the quadriceps muscle group and interiorly, it is attached to the patellar ligament 42, which inserts into the anterior surface of the tibia 44. The patella functions to enhance the lever arm of the muscles which extend the leg. As such, the patella is loaded in tension, having an approximate superior-inferior direction.

When the patella is fractured in a transverse direction, perpendicular to the line of force, apposition of the patella fragments and compressive force is required to keep the fragments in close approximation for healing. Generally, surgical wire has been used to bend tightly around the patella, twisting two ends of a wire together to provide compressive force. This application method often results in wire breakage. In addition, post implantation wire fatigue caused by high tensile stresses from the quadriceps muscle group during extension of the leg often causes surgical wire to fail. Failure of the wire to apply sufficient compressive force or failure or intimate apposition of patella fragments due to wire breakage results in a reduced or failed healing of the bone. Sharp wire points caused by wire breakage in situ can result in significant damage to surrounding tissues and may even penetrate the knee joint capsule.

The load bearing cable 10 of the present invention is substituted for surgical wire in repair of patella fractures. The cable material is wrapped tightly around the patella 40 with two ends 46 tied together tightly to provide compressive force. The cable has sufficient tensile strength to maintain the patella fragments in close approximation and promote active healing, and is sufficiently inelastic to prevent separation of the patella fragments under tensile loading. The load bearing cable is less susceptible to fatigue failure than surgical wire. In the event the cable does fail, no threat of damage to surrounding tissues is posed.

When the cable is formed of a bioresorbable polymeric fiber, stress will gradually be transferred to the patella in a controlled manner, as the cable is resorbed, enhancing healing per Wolff's law, bone remodels in response to applied stress.

EXAMPLE 6

FUSION OF SPINAL VERTEBRAE

Current procedures for repair or fusion of the spinal column restrict motion of vertebral bodies by fixing posterior elements of the vertebrae, transverse processes and pedicles, together, inserting a bone graft along the posterior surface of the spinal column, and then fixing the graft into position. Satisfactory fusion requires that the vertebrae remain sufficiently immobilized to permit healing of the bone graft to the vertebrae.

In general, surgical wire has been used in this procedure. Problems with the use of surgical wire in spinal fusions are similar to those encountered with the patella fusion described for Example 5, including wire breakage during insertion or tensioning, failure to maintain adequate compressive force, and fatigue of wire over time. In addition the proximity of the spinal cord to the fusion site makes the consequences of wire breakage life threatening.

These problems are circumvented by use of the load bearing cable of the present invention as described in Example 5. As shown, for example in FIG. 1, the surgical cable 10 of the present invention is substituted for surgical wire in the fixation of the posterior elements 50 of the vertebrae and fixation of the graft into position. The surgical cable of the present invention provides sufficient compression and tensile strength to maintain the vertebral processes and/or graft in close approximation for fusion and healing.

When a bioresorbable fiber cable is used, stresses transferred to the bone graft in a controlled manner as the cable is resorbed, resulting in enhanced healing and greater success rate.

Having described the invention above, various modifications of the techniques, procedures, material and equipment will be apparent to those in the art. It is intended that all such variations within the scope and spirit of the appended claims be embraced thereby.

We claim:

1. A method for the fusion of bone segments having outer surfaces, comprising the steps of:

(a) positioning the bone segments into close approximation with each other;

(b) providing a surgical cable formed of a plurality of polymeric fibers to force the opposed bone segments toward each other, the polymeric cable having two free ends and being of a diameter of between one and three millimeters (1–3 mm) along the entire length thereof including said ends, to define an elongated thin cable with sufficient inherent flexibility for enabling the cable to be wrapped around the bone segments, said cable having fibers with sufficient tensile strength so that the cable is capable of bearing stress loads to allow the fusion of the said opposing bone segments and to be sufficiently inelastic so as to maintain continuous pressure on the bone segments;

b) wrapping the cable around the bone segments;

c) applying a compressive force to the adjacent bone segments;

(d) securing the cable in place relative to the bone segments by joining the cable ends together; and e) minimizing stress concentration at the bone segment outer surfaces by closely conforming the cable to the outer surfaces of the bone segments.

2. The method of claim 1, wherein the cable having a diameter of 3 millimeters or less has a tensile strength of generally 310,000 psi which provides a load bearing capacity of about 1600 pounds.

3. The method of claim 1, wherein the opposed bone elements includes adjacent vertebrae of a spinal column.

4. The method of claim 1, wherein the polymeric cable is formed from a plurality of polymeric fibers with the tensile strength of each polymeric fiber being greater than 350,000 psi.

5. The method of claim 1, wherein the cable has a diameter of 3 millimeters or less with a tensile strength of generally 310,000 psi which provides a load bearing capacity of about 1600 pounds.

6. The method of claim 1, wherein the polymeric cable is formed of braided strands of polymeric fiber.

7. The method of claim 1, wherein the polymeric material is formed of ultra high molecular weight polyethylene fibers.

8. The method of claim 7, wherein the polymeric fibers are formed of Spectra 1000 (T).

9. The method of claim 1, wherein the polymeric material is biocompatible.

10. The method of claim 1, wherein the step of securing the cable further includes knotting the ends of the cable together.

11. The method of claim 1, wherein the step of securing the cable further includes fusing the ends of the cable together with heat.

12. The method of claim 1, wherein the step of securing the cable further includes attachment to bone with an attachment means, the attachment means is selected from the group consisting of surgical staples, pins, and screws.

13. A method for the fusion of vertebrae of a spinal column, comprising the steps of:

(a) providing a surgical cable formed of a plurality of polymeric fibers to force the vertebrae toward each other, the polymeric cable having two free ends and being of a diameter of between one and three millimeters (-3 mm) along the entire length thereof including said ends to define an elongated thin cable with sufficient inherent flexibility for enabling the cable to be wrapped around the vertebrae fragments, said cable having fibers with sufficient tensile strength, so that the cable is capable of bearing sufficient stress loads to allow the fusion of adjacent vertebrae; and b) wrapping the cable around the vertebrae;

c) applying a compressive force to the adjacent vertebrae;

d) securing the cable in place relative to the vertebrae by joining the cable ends together; and e) minimizing stress concentration by closely conforming the cable to the outer surface vertebrae.

14. The method of claim 13, wherein the polymeric cable is formed from a plurality of polymeric fibers having a diameter of less than or equal to 3 millimeters with the tensile strength of each polymeric fiber being no less than about 350,000 psi.

15. The method of claim 13, wherein the polymeric cable is formed of braided strands of polymeric fiber.

16. The method of claim 13, wherein the polymeric material is formed of ultra high molecular weight polyethylene fibers.

17. The method of claim 16, wherein the polymeric fibers are formed of Spectra 1000™.

18. The method of claim 13, wherein the polymeric material is biocompatible.

19. The method of claim 13, wherein the step of securing the cable further includes knotting the ends of the cable together.

20. The method of claim 13, wherein the step of securing the cable further includes fusing the ends of the cable together with heat.

21. The method of claim 13, wherein the step of securing the cable further includes attachment to bone with an attachment means, the attachment means is selected from the group consisting of staples, pins, and screws.

* * * * *